(12) United States Patent
Covach et al.

(10) Patent No.: US 9,820,742 B2
(45) Date of Patent: Nov. 21, 2017

(54) SURGICAL STAPLER WITH EXPANDABLE JAW

(71) Applicant: Applied Medical Resources Corporation, Rancho Santa Margarita, CA (US)

(72) Inventors: Jonathan Covach, Rancho Santa Margarita, CA (US); Matthew M. Becerra, Rancho Santa Margarita, CA (US); Gary M. Johnson, Rancho Santa Margarita, CA (US)

(73) Assignee: Applied Medical Resources Corporation, Rancho Santa Magarita, CA (US)

( * ) Notice: Subject to any disclaimer, the term of this patent is extended or adjusted under 35 U.S.C. 154(b) by 803 days.

(21) Appl. No.: 14/211,570

(22) Filed: Mar. 14, 2014

(65) Prior Publication Data

US 2014/0263540 A1    Sep. 18, 2014

Related U.S. Application Data

(60) Provisional application No. 61/793,065, filed on Mar. 15, 2013.

(51) Int. Cl.
*A61B 17/068* (2006.01)
*A61B 17/072* (2006.01)
*A61B 17/00* (2006.01)

(52) U.S. Cl.
CPC ...... *A61B 17/07207* (2013.01); *A61B 2017/0046* (2013.01); *A61B 2017/00477* (2013.01); *A61B 2017/07257* (2013.01)

(58) Field of Classification Search
CPC .... A61B 17/07207; A61B 2017/07257; A61B 2017/00477; A61B 2017/0046
See application file for complete search history.

(56) References Cited

U.S. PATENT DOCUMENTS

| 3,494,533 A | 2/1970 | Green et al. |
| 4,608,981 A | 9/1986 | Rothfuss et al. |

(Continued)

FOREIGN PATENT DOCUMENTS

RU    2063710    7/1996

OTHER PUBLICATIONS

The International Bureau of WIPO, International Preliminary Report on Patentability, dated Sep. 24, 2015, for International Application No. PCT/US2014/027768.

International Searching Authority, U.S., The International Search Report and the Written Opinion of the International Searching authority for International application PCT/US2014/027768, titled "Surgical Stapler with Expandable Jaw", dated Jul. 25, 2014.

(Continued)

*Primary Examiner* — Thanh Truong
*Assistant Examiner* — Thomas Wittenschlaeger
(74) *Attorney, Agent, or Firm* — John F. Heal

(57) ABSTRACT

Jaw assemblies for a surgical stapler are provided. The jaw assemblies comprise a first jaw having a first clamping surface and a plurality of staples disposed therein and second jaw assembly having a second clamping surface. The jaw assemblies can be actuated from a closed configuration in which the first clamping surface contacts or is adjacent to the second clamping surface to an open configuration in which the second jaw is pivoted away from the first jaw to a stapling position in which the second clamping surface is parallel to the first clamping surface and spaced apart from the first clamping surface. A pivoting link or sliding pivot joint can couple the second jaw to the first jaw to facilitate motion between the closed position, the open position, and the stapling position.

5 Claims, 12 Drawing Sheets

(56) References Cited

U.S. PATENT DOCUMENTS

| | | | | |
|---|---|---|---|---|
| 5,364,001 | A | * | 11/1994 | Bryan ............... A61B 17/07207 227/175.1 |
| 5,413,268 | A | * | 5/1995 | Green ............... A61B 17/07207 227/176.1 |
| 5,433,721 | A | * | 7/1995 | Hooven ............... A61B 17/072 227/175.1 |
| 5,447,265 | A | | 9/1995 | Vidal et al. |
| 5,489,058 | A | | 2/1996 | Plyley |
| 5,697,542 | A | * | 12/1997 | Knodel ............ A61B 17/07207 227/175.1 |
| 6,716,232 | B1 | * | 4/2004 | Vidal ............... A61B 17/07207 227/176.1 |
| 7,617,961 | B2 | * | 11/2009 | Viola ............... A61B 17/07207 227/175.1 |
| 7,651,017 | B2 | | 1/2010 | Ortiz et al. |
| 7,845,534 | B2 | | 12/2010 | Viola et al. |
| 8,596,513 | B2 | | 12/2013 | Olson |
| 2002/0062136 | A1 | | 5/2002 | Hillstead |
| 2006/0235442 | A1 | | 10/2006 | Huitema |
| 2011/0290851 | A1 | * | 12/2011 | Shelton, IV ..... A61B 17/07207 227/176.1 |
| 2013/0056521 | A1 | | 3/2013 | Swensgard |
| 2013/0240604 | A1 | | 9/2013 | Knodel |

OTHER PUBLICATIONS

European Patent Office, Partial European Search Report for European Application No. EP 14762896.0, entitled "Surgical Stapler With Expandable Jaw," dated Apr. 10, 2017, 6 pgs.

\* cited by examiner

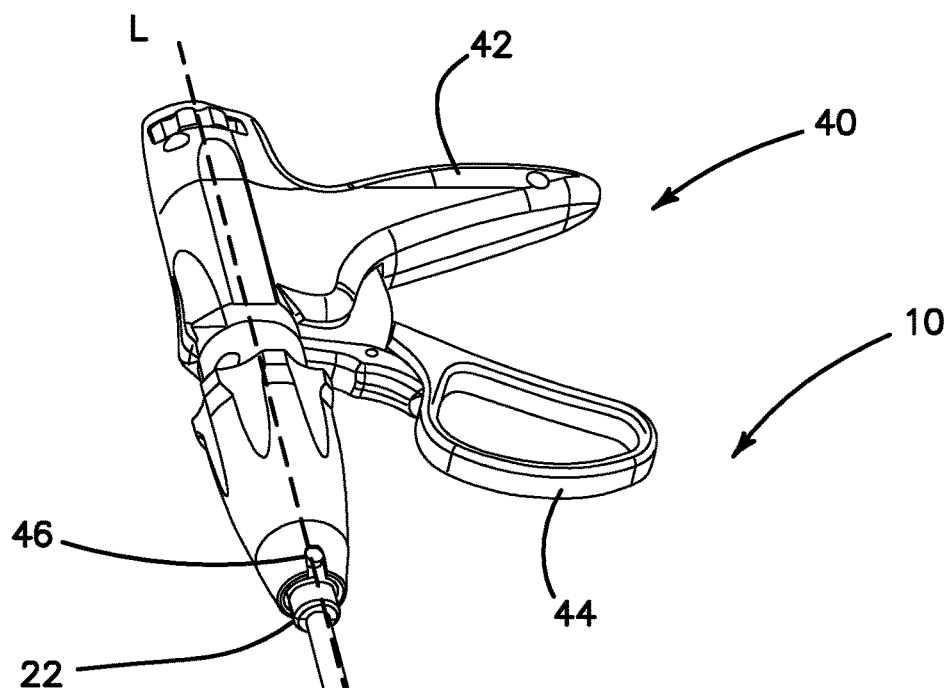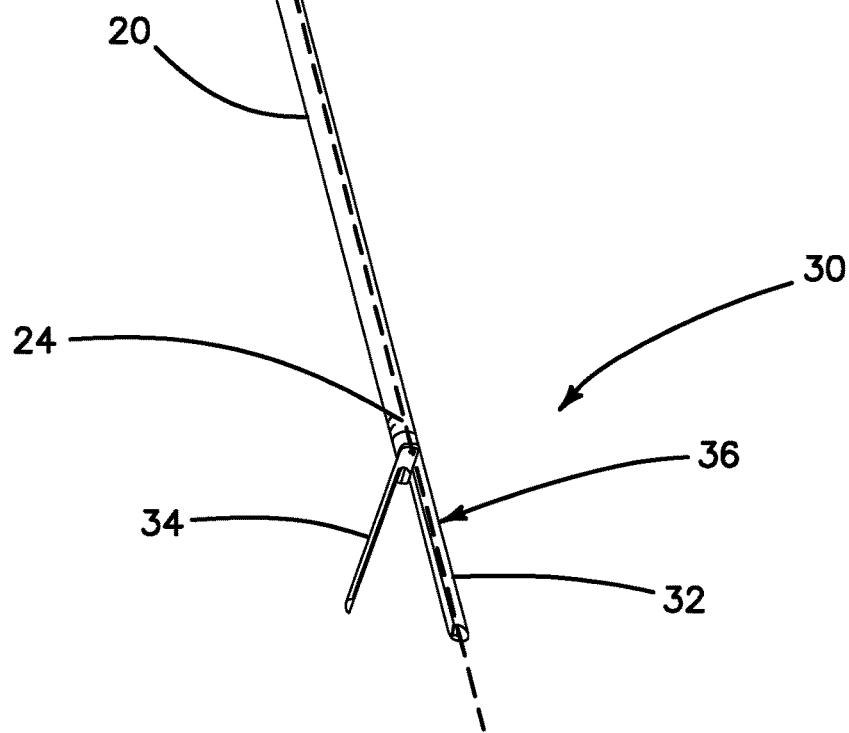
FIG. 1

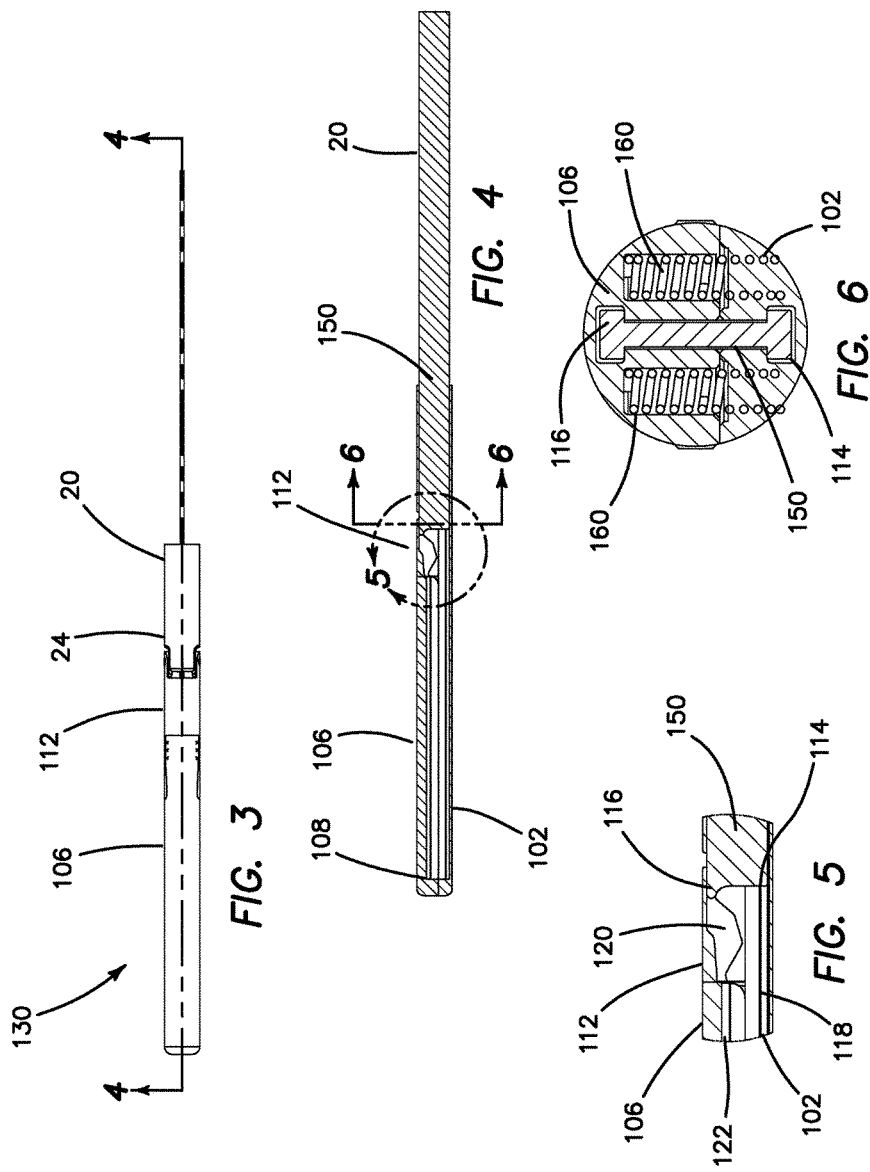

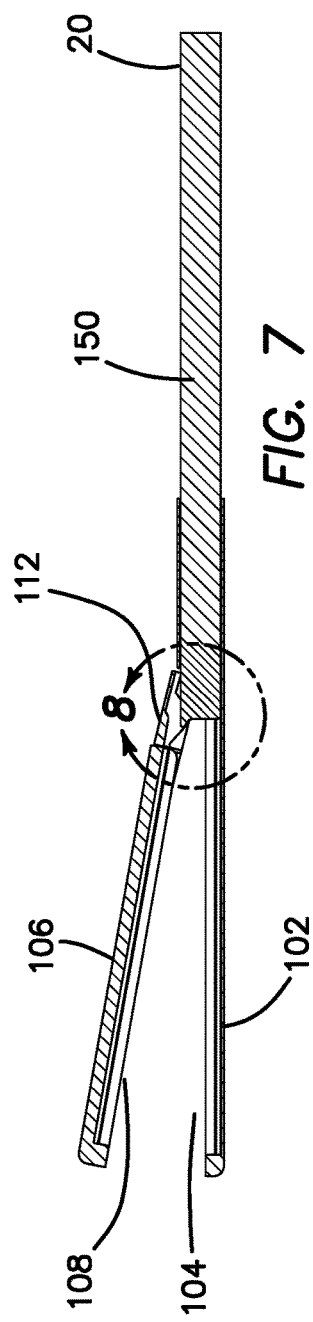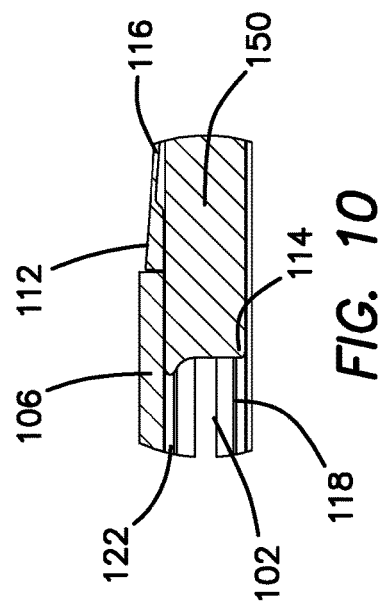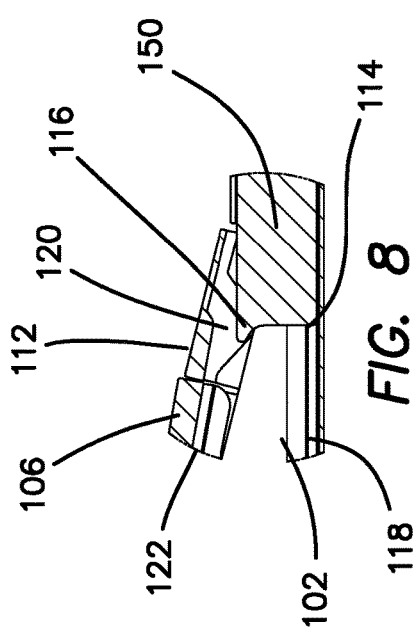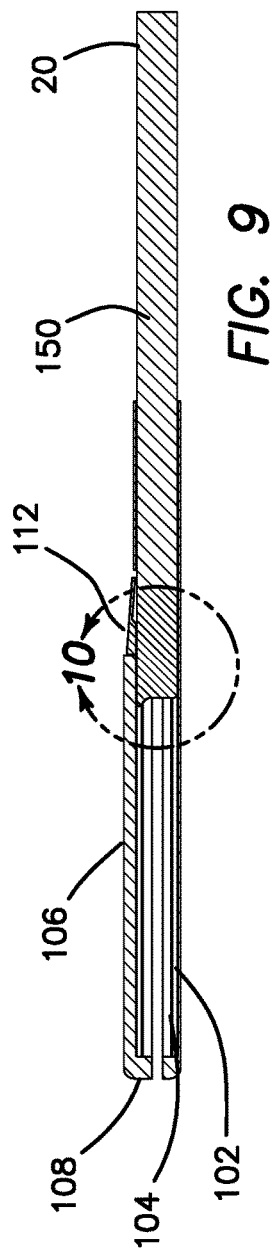

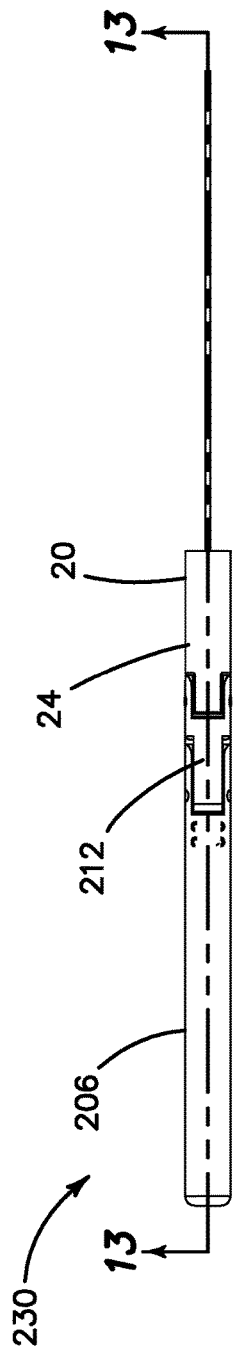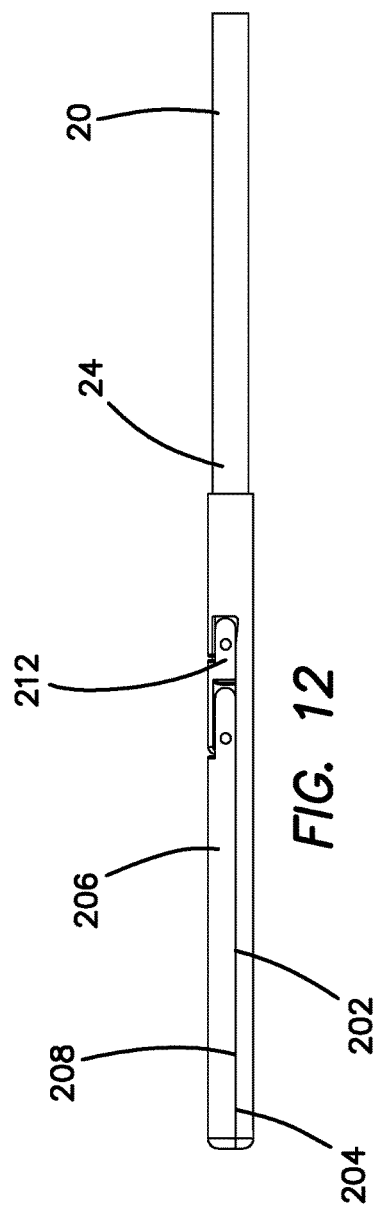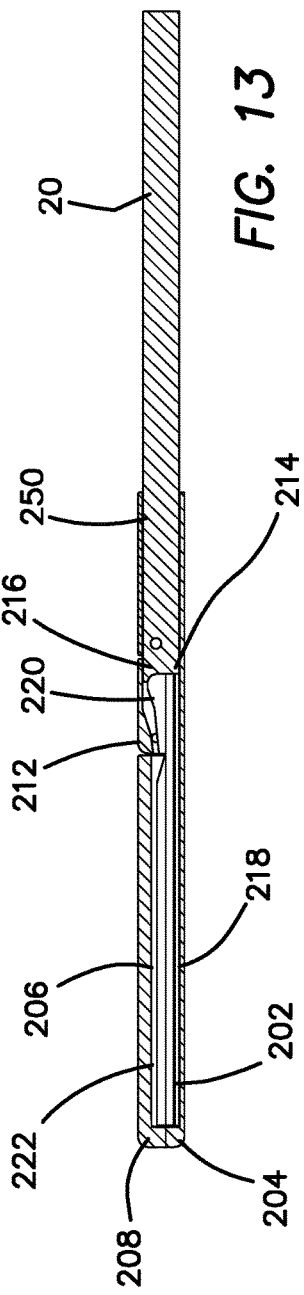

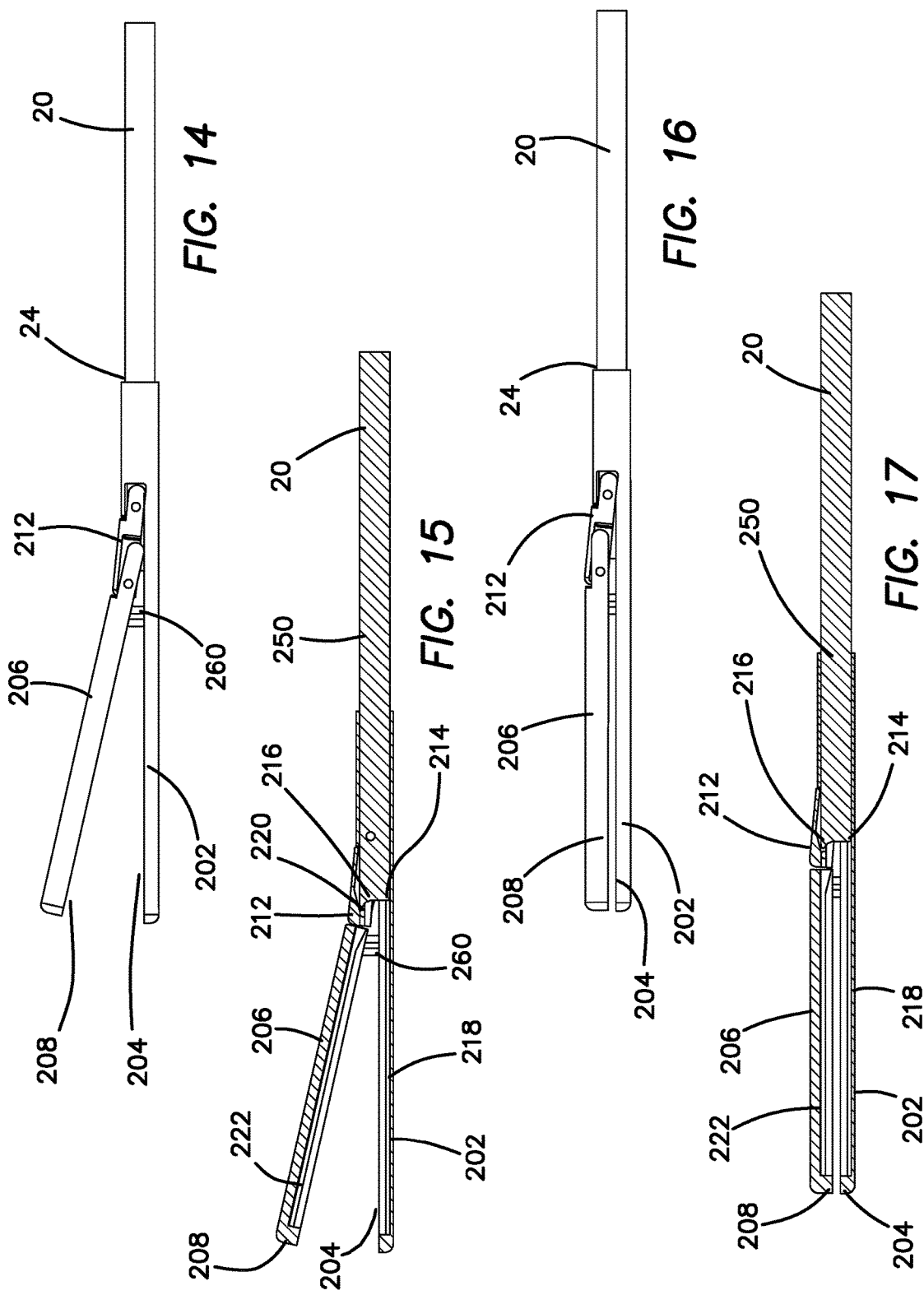

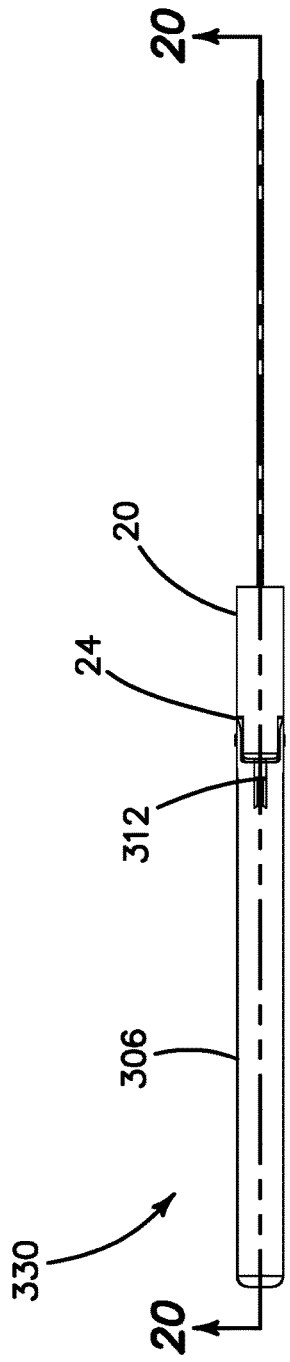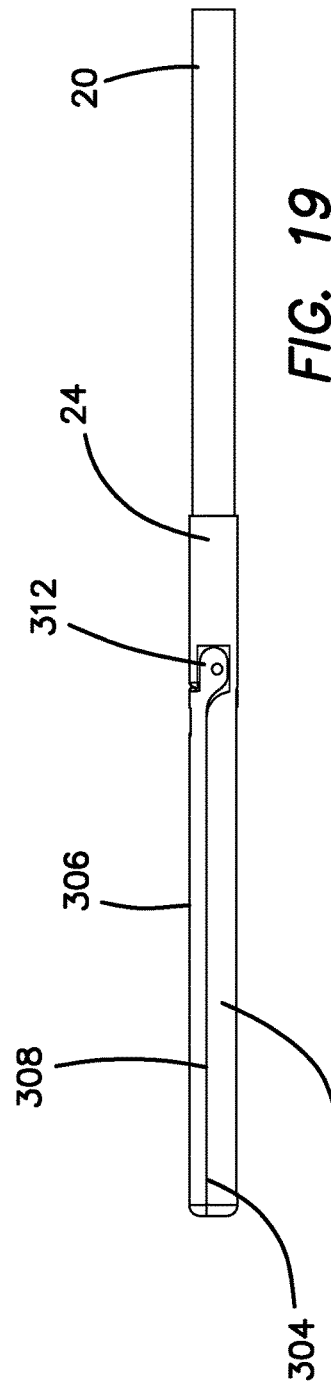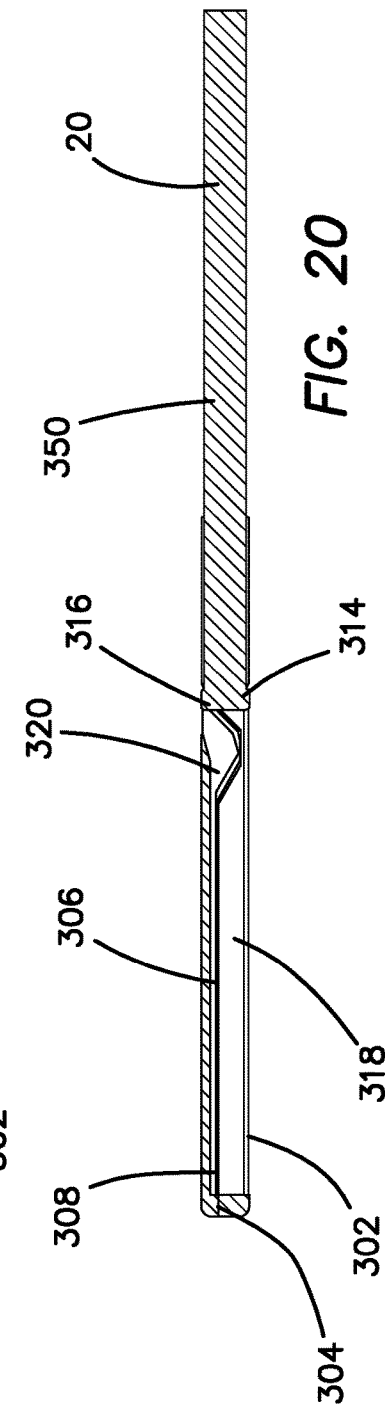

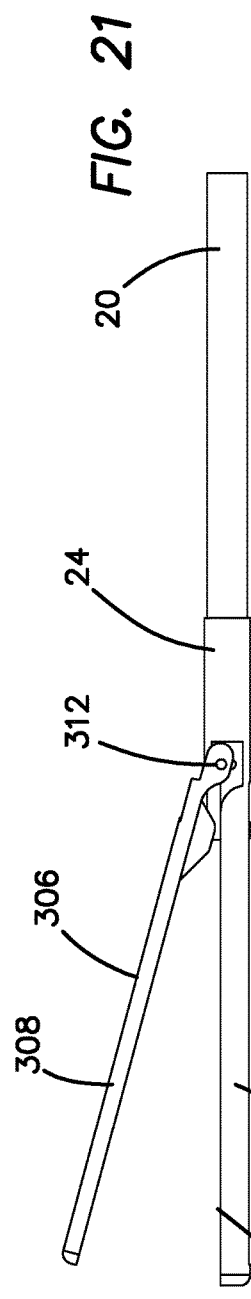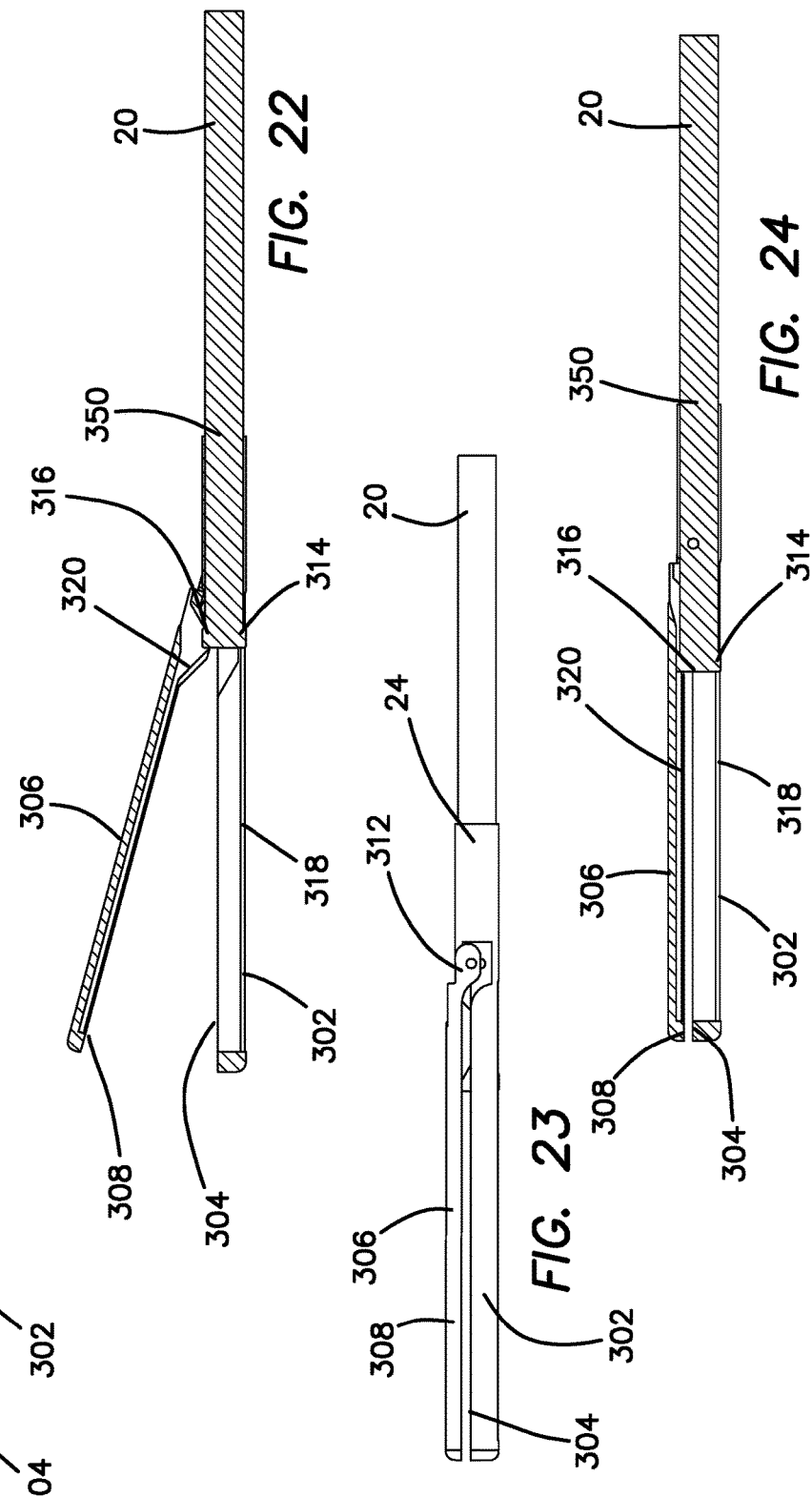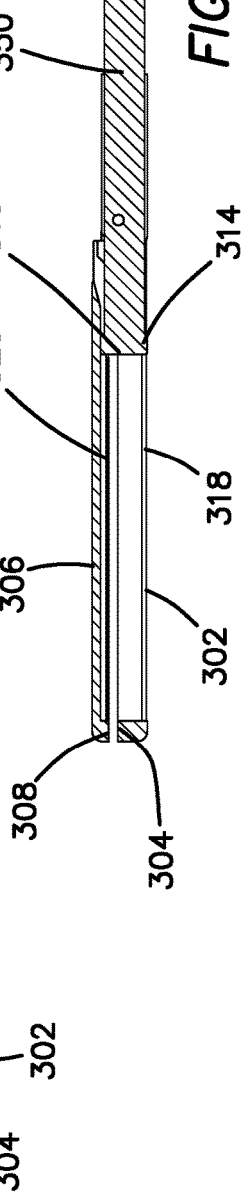

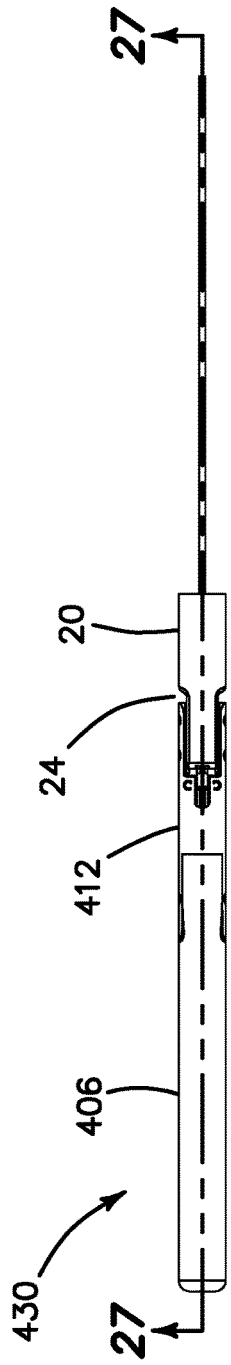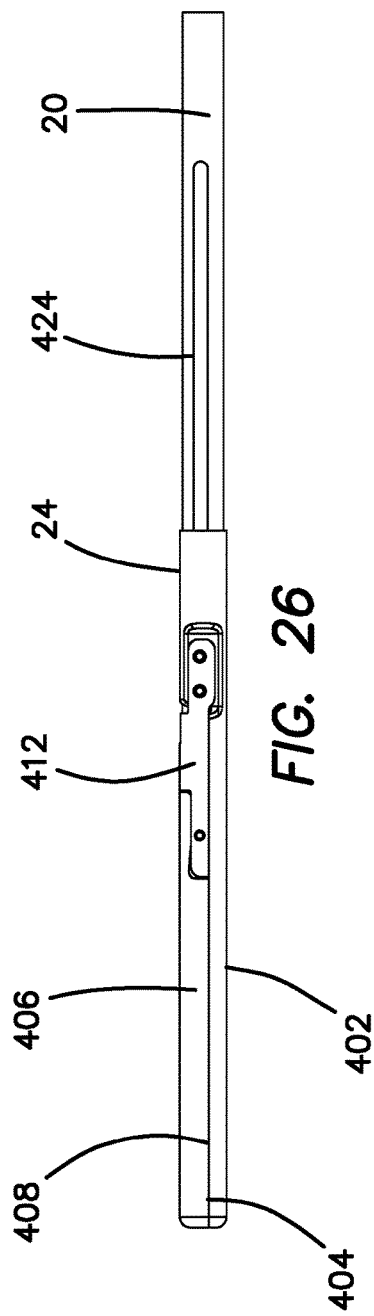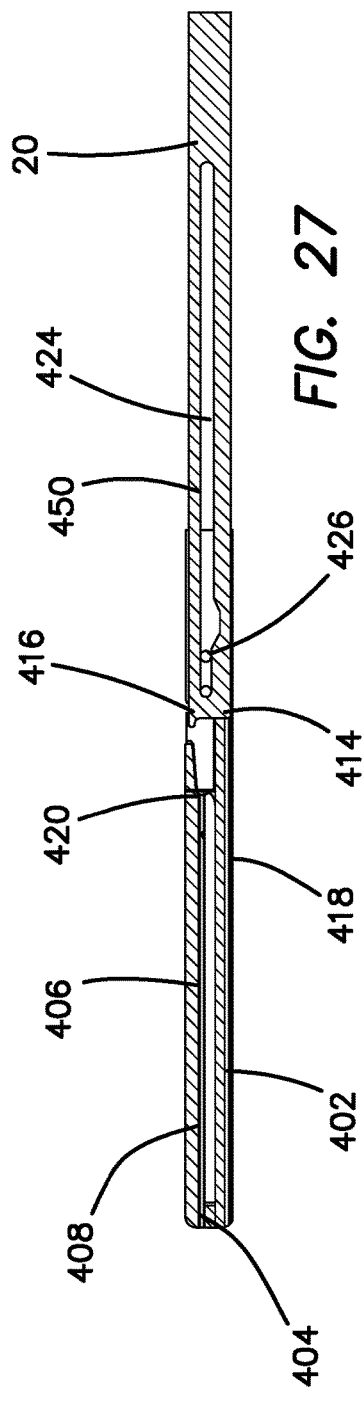

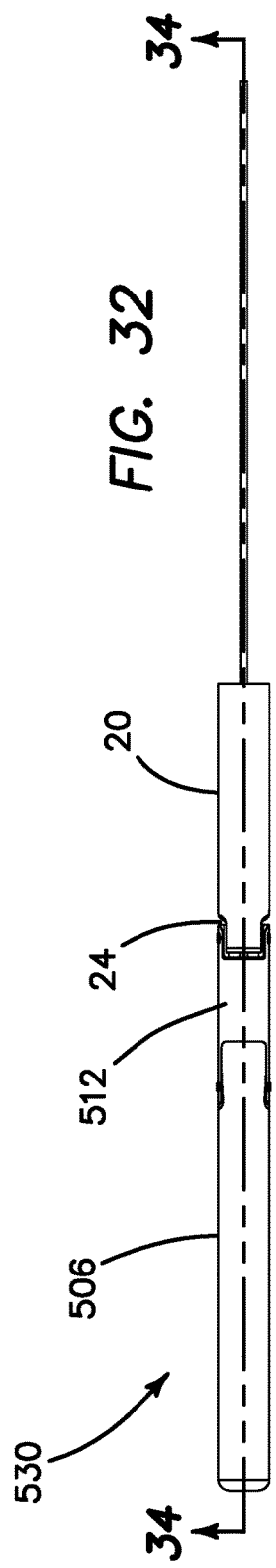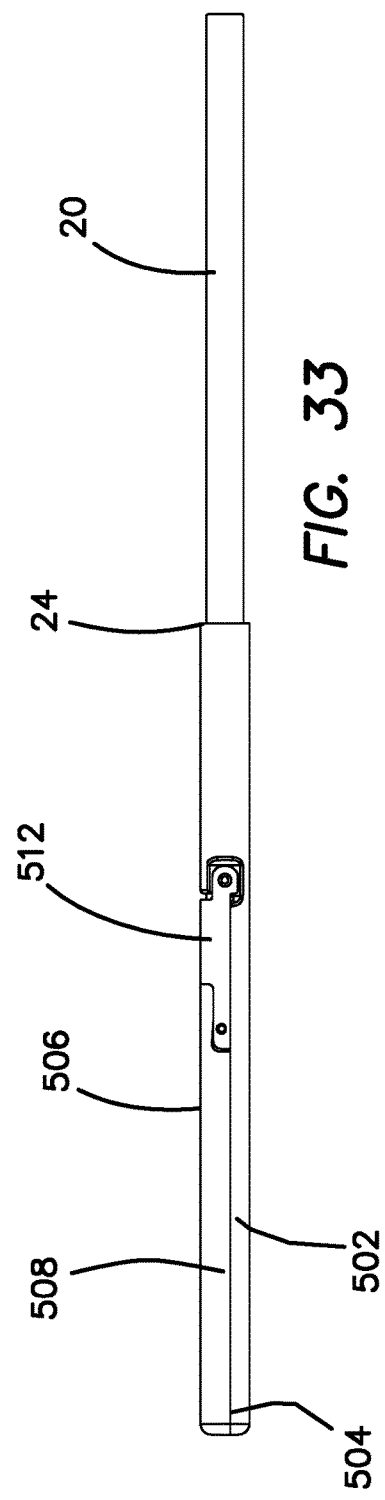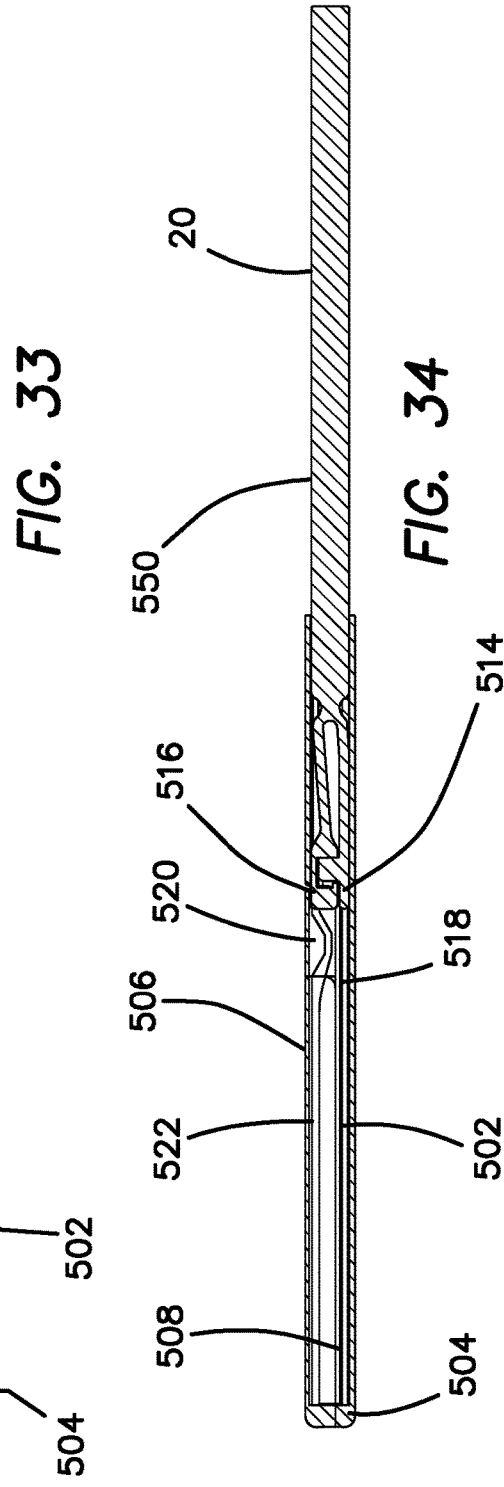

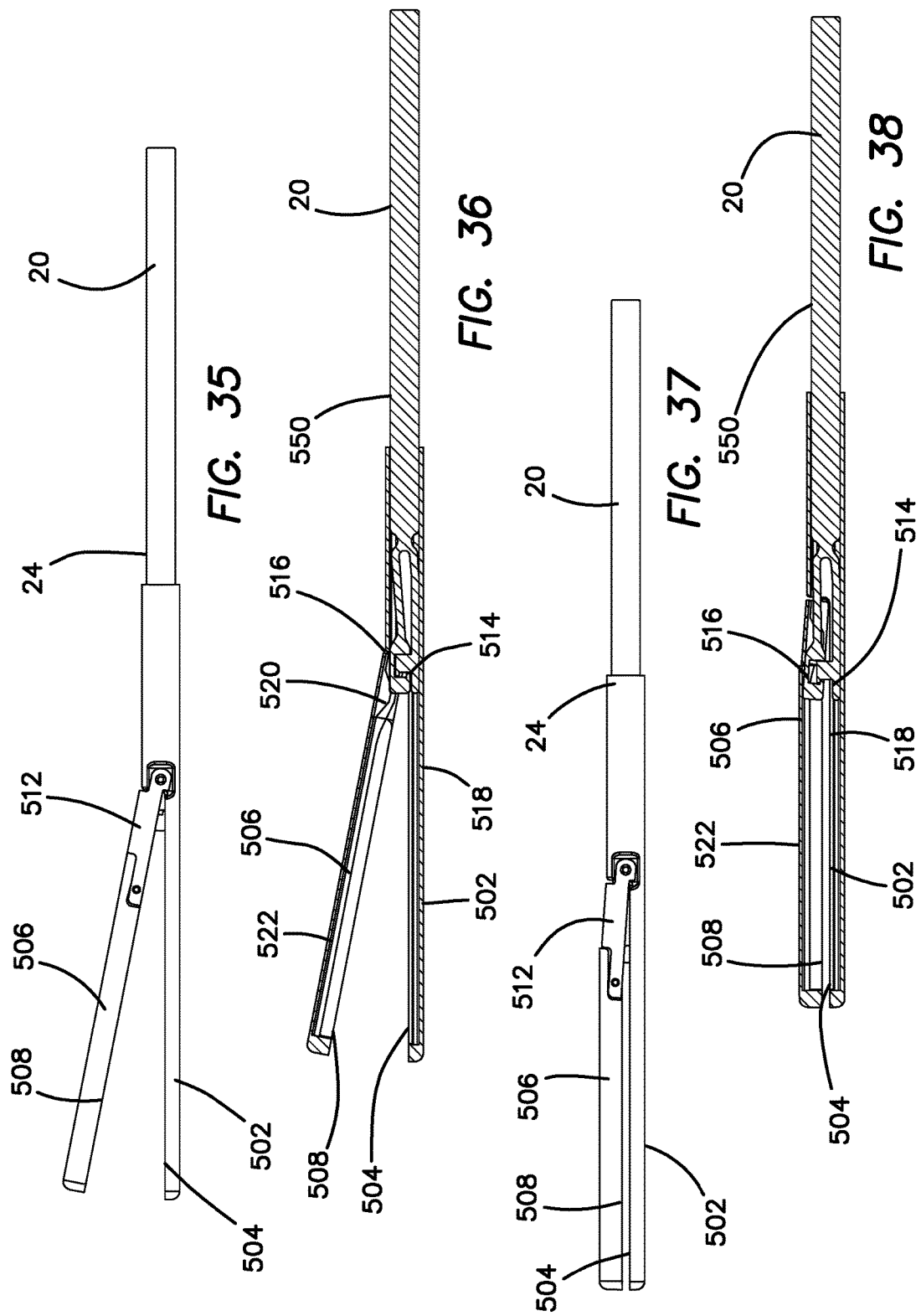

SURGICAL STAPLER WITH EXPANDABLE JAW

CROSS REFERENCE TO RELATED APPLICATIONS

This application claims the benefit of U.S. Provisional Patent Application Ser. No. 61/793,065, entitled "SURGICAL STAPLER WITH EXPANDABLE JAW," filed on Mar. 15, 2013. The entirety of this prior application is hereby incorporated herein by reference.

BACKGROUND OF THE INVENTION

Field of the Invention

The present application relates generally to surgical occlusion instruments and, more particularly, to surgical staplers.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

SUMMARY OF THE INVENTION

In certain embodiments, a surgical stapler is provided herein. The surgical stapler comprises an elongate shaft, a handle assembly, an actuation mechanism, and a jaw assembly. The elongate shaft has a proximal end and a distal end and defines a longitudinal axis between the proximal end and the distal end. The handle assembly is disposed at the proximal end of the elongate shaft. The actuation mechanism is actuatable by the handle assembly. The actuation mechanism comprises an actuation beam extending through at least a portion of the elongate shaft. The jaw assembly is disposed at the distal end of the elongate shaft. The jaw assembly comprises a first jaw, a second jaw, and a plurality of staples positioned in the first jaw. The first jaw defines a first clamping surface. The second jaw defines a second clamping surface. The jaw assembly is actuatable by longitudinal movement of the actuation beam between a closed position in which the first clamping surface contacts the second clamping surface, an open position in which the second clamping surface extends at an angle transverse to the first clamping surface, and a stapling position in which the first clamping surface extends parallel to the second clamping surface and is spaced apart from the second clamping surface.

In certain embodiments, a surgical stapler is provided herein. The surgical stapler comprises an elongate shaft, a handle assembly, an actuation mechanism, and a jaw assembly. The elongate shaft has a proximal end and a distal end and defines a longitudinal axis between the proximal end and the distal end. The handle assembly is disposed at the proximal end of the elongate shaft. The actuation mechanism is actuatable by the handle assembly. The actuation mechanism comprises an actuation member extending through at least a portion of the elongate shaft. The actuation member comprises a first guide and a second guide thereon. The jaw assembly is disposed at the distal end of the elongate shaft. The jaw assembly comprises a first jaw, a link, and a second jaw. The first jaw extends distally from the distal end of the elongate shaft. The first jaw comprises a first guide slot extending longitudinally therein. The link has a proximal end and a distal end. The link comprises a second guide slot having a ramped opening profile formed therein. The proximal end of the link is pivotably coupled to the distal end of the elongate shaft. The second jaw extends distally from the distal end of the link. The second jaw is pivotably coupled to the distal end of the link. The second jaw comprises a third guide slot extending longitudinally therein. A plurality of staples is disposed in the first jaw. The first guide is slideable in the first guide slot and the second guide is slideable in the second guide slot and the third guide slot. Translation of the second guide distally over the ramped opening profile of the second guide slot pivots the link away from the first jaw to define an open position of the jaw assembly.

In certain embodiments, a surgical stapler is provided herein. The surgical stapler comprises an elongate shaft, a handle assembly, an actuation mechanism, and a jaw assembly. The elongate shaft has a proximal end and a distal end and defines a longitudinal axis between the proximal end and the distal end. The handle assembly is disposed at the proximal end of the elongate shaft. The actuation mechanism is actuatable by the handle assembly. The actuation mechanism comprises an actuation member extending through at least a portion of the elongate shaft. The actuation member comprises a first guide and a second guide thereon. The jaw assembly is disposed at the distal end of the elongate shaft. The jaw assembly comprises a first jaw, a second jaw, and a plurality of staples. The first jaw extends distally from the distal end of the elongate shaft. The first jaw comprises a first guide slot extending longitudinally therein and a first clamping surface. The second jaw comprises a second guide slot and a second clamping surface. The second guide slot extends in the second jaw. The second guide slot has an opening segment with a ramped profile and a stapling segment extending generally longitudinally distal of the opening segment. The second jaw is slideably coupled to the distal end of the elongate shaft such that it is movable between a closed position in which the first clamping surface contacts the second clamping surface and a stapling position in which the first clamping surface is parallel to and spaced from the second clamping surface. The second jaw is pivotably coupled to the distal end of the elongate shaft such that the first jaw is pivotable from the closed position to an open position in which the second clamping surface extends at an angle transverse to the first clamping surface. The first guide is slideable in the first guide slot and the second guide is slideable in the second guide slot such that translation of the second guide distally through the open segment of the second guide slot slides and pivots the second jaw from the closed position to the open position, and translation of the second guide distally through the stapling segment positions the second jaw in the stapling position.

BRIEF DESCRIPTION OF THE DRAWINGS

FIG. 1 is a perspective view of an embodiment of surgical stapling device with the jaws in an open configuration;

FIG. 3 is a top view of an embodiment of jaw assembly for use in a surgical stapler with the jaws in a closed configuration;

FIG. 4 is a cross-sectional side view of the jaw assembly of FIG. 3;

FIG. 5 is a detailed cross-sectional side view of the jaw assembly of FIG. 3;

FIG. 6 is a detailed cross-sectional end view of the jaw assembly of FIG. 3;

FIG. 7 is a cross-sectional side view of the jaw assembly of FIG. 3 with the jaws in an open configuration;

FIG. 8 is a detailed cross-sectional side view of the jaw assembly of FIG. 3 with the jaws in the open configuration;

FIG. 9 is a cross-sectional side view of the jaw assembly of FIG. 3 with the jaws in a firing configuration;

FIG. 10 is a detailed cross-sectional side view of the jaw assembly of FIG. 3 with the jaws in the firing configuration;

FIG. 11 is a top view of an embodiment of jaw assembly for use in a surgical stapler with the jaws in a closed configuration;

FIG. 12 is a side view of the jaw assembly of FIG. 11;

FIG. 13 is a cross-sectional side view of the jaw assembly FIG. 11;

FIG. 14 is a side view of the jaw assembly of FIG. 11 with the jaws in an open configuration;

FIG. 15 is a cross-sectional side view of the jaw assembly of FIG. 11 with the jaws in the open configuration;

FIG. 16 is a side view of the jaw assembly of FIG. 11 with the jaws in a firing configuration;

FIG. 17 is a cross-sectional side view of the jaw assembly of FIG. 11 with the jaws in a firing configuration;

FIG. 18 is a top view of an embodiment of jaw assembly for use in a surgical stapler with the jaws in a closed configuration;

FIG. 19 is a side view of the jaw assembly of FIG. 18;

FIG. 20 is a cross-sectional side view of the jaw assembly of FIG. 18;

FIG. 21 is a side view of the jaw assembly of FIG. 18 with the jaws in an open configuration;

FIG. 22 is a cross-sectional side view of the jaw assembly FIG. 18 with the jaws in the open configuration;

FIG. 23 is a side view of the jaw assembly of FIG. 18 with the jaws in a firing configuration;

FIG. 24 is a cross-sectional side view of the jaw assembly of FIG. 18 with the jaws in the firing configuration;

FIG. 25 is a top view of an embodiment of jaw assembly for use in the surgical stapler with the jaws in a closed configuration;

FIG. 26 is a side view of the jaw assembly of FIG. 25;

FIG. 27 is a side cross-sectional view of the jaw assembly of FIG. 25;

FIG. 32 is a top view of an embodiment of jaw assembly for use in a surgical stapler with jaws in a closed configuration;

FIG. 33 is a side view of the jaw assembly of FIG. 32;

FIG. 34 is a cross-sectional side view of the jaw assembly of FIG. 32;

FIG. 35 is a side view of the jaw assembly of FIG. 32 with the jaws in an open configuration;

FIG. 36 is a cross-sectional side view of the jaw assembly of FIG. 32 with the jaws in the open configuration;

FIG. 37 is a side view of the jaw assembly of FIG. 32 with the jaws in a firing configuration;

FIG. 38 is a cross-sectional side view of the jaw assembly of FIG. 32 with the jaws in the firing configuration;

DETAILED DESCRIPTION OF THE INVENTION

Figure 2:
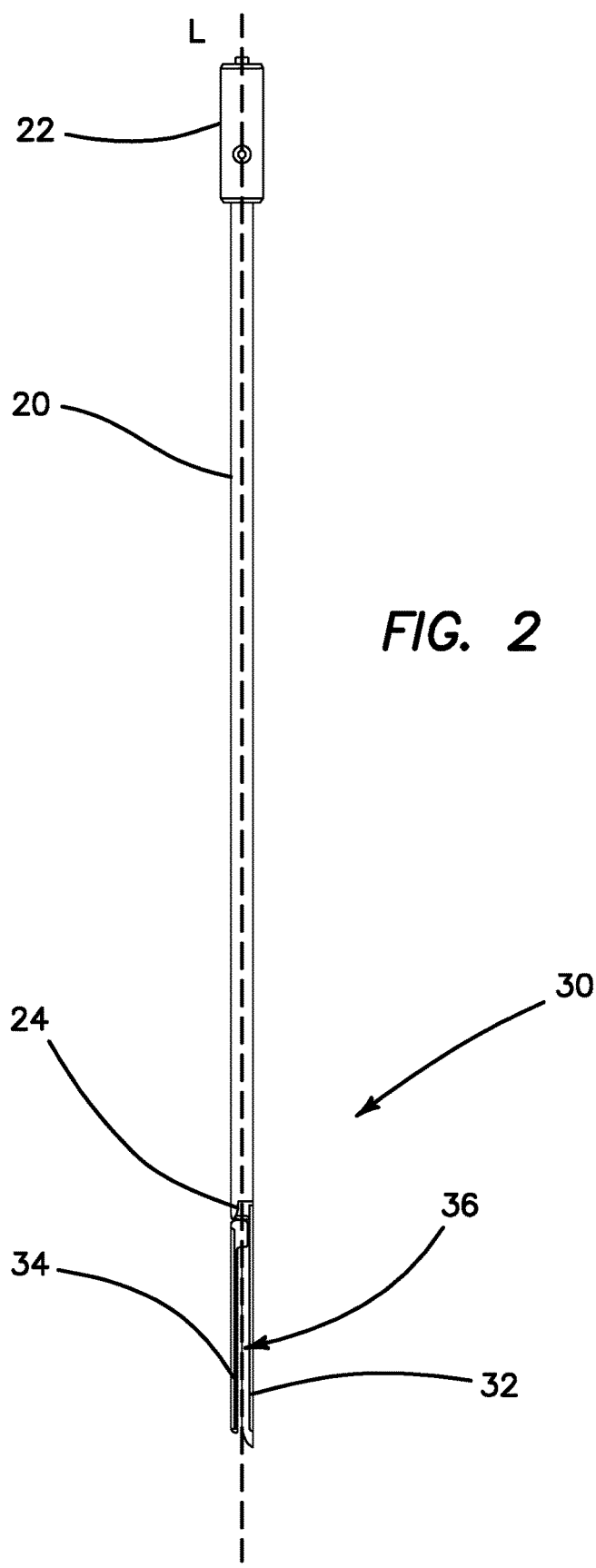
FIG. 2 is a perspective view of an embodiment of cartridge including an elongate shaft and a jaw assembly for the surgical stapling device of FIG. 1 with the jaws in a closed configuration.

With reference to FIGS. 1-2, an embodiment of surgical stapling device is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration. FIG. 2 illustrates a removable cartridge of the surgical stapler 10 with a jaw assembly 30 in a closed configuration.

With continued reference to FIGS. 1 and 2, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIGS. 1 and 2, as illustrated, the elongate shaft 20 comprises a generally tubular member. The elongate shaft 20 extends from a proximal end 22 to a distal end 24. Elongate shaft 20 defines a central longitudinal axis, L. of the surgical stapler 10 extending between the proximal end 22 and the distal end 24.

With continued reference to FIGS. 1 and 2, in the illustrated embodiment, the jaw assembly 30 is coupled to the elongate shaft 20 at the distal end 24 of the elongate shaft 20. The jaw assembly 30 comprises a first jaw 32 and a second jaw 34 pivotally coupled to the first jaw 32. In the illustrated embodiment, the first jaw 32 is fixed to the distal end 24 of elongate shaft 20 such that it extends distally along the central longitudinal axis, L and remains stationary with respect to the elongate shaft 20. In other embodiments, it is contemplated that the jaw assembly 30 is articulable with respect to the elongate shaft 20. In an initial configuration, the first jaw 32 includes a plurality of staples 36 disposed therein. In some embodiments, staples can be initially positioned in the second jaw 34.

With continued reference to FIGS. 1 and 2, in the illustrated embodiment, the jaw assembly 30 can be actuated from an open configuration (FIG. 1) to a closed configuration (FIG. 2) to a stapling configuration by an actuation member or beam that is longitudinally slideable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the first jaw 32.

With continued reference to FIGS. 1 and 2, in the illustrated embodiment, the handle assembly is coupled to the elongate shaft 20 at the proximal end 22 of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configurations such as, for example, scissors-grip configurations, or in-line configurations. As further described in greater detail below, the handle assembly 40 houses an actuation mechanism configured to selectively advance an actuation shaft responsive to movement of the movable handle 44.

In some embodiments, the surgical stapler 10 can include the plurality of staples 36 positioned in a disposable cartridge while the handle assembly 40 is configured to be reused with multiple staple cartridges. In the illustrated embodiment, the elongate shaft 20 and jaw assembly 30 define a disposable cartridge that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10 The coupler 46 can a bayonet connection having an outer connector that can removably couple to handle assembly 42 the elongate shaft 20, and an inner connector that can removably couple the actuation shaft of the handle assembly 42 to the actuation member of the elongate shaft 20. Accordingly, the surgical stapler 10 can be configured such that the handle assembly 40 can be reused with multiple disposable cartridges during a surgical procedure. It is contemplated that in other embodiments, the handle assembly and some portion of the elongate shaft can be reusable while a remainder of the elongate shaft in the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable.

As discussed above, surgical staplers 10 described herein can be sized and configured for insertion into a surgical site through a relatively small diameter trocar cannula such as a so-called 5 mm trocar cannula having a working channel inner diameter smaller than about 8 mm. Desirably, jaw assemblies configured for insertion through a 5 mm trocar cannula efficiently employ the relatively limited working space to position both jaws, a plurality of staples, and staple firing elements. In a jaw assembly for a typical laparoscopic surgical stapler, with the jaw assembly in a closed or firing configuration, the first jaw is spaced apart from the second jaw by a gap to accommodate tissue clamped therebetween when the stapler is in use. However, in a jaw assembly configured for insertion through 5 mm trocar cannula, this spacing of the first jaw from the second jaw in the closed position can undesirably be wasted working space. Accordingly, it can be desirable to configure operation of a jaw assembly configured for insertion through a 5 mm trocar cannula such that the gap that would otherwise be wasted working space is repurposed to enhance stapling performance. For example, in a jaw assembly configured to eliminate the gap, the otherwise wasted working space can be repurposed to provide larger staples or more robust staple driving hardware. In various embodiments, jaw assemblies are provided herein that reduce or eliminate the gap between the first jaw and the second jaw in a closed configuration such that the working space of a relatively small diameter surgical stapler can be maximized.

With reference to FIGS. 3-10, an embodiment of jaw assembly 130 is illustrated. FIG. 3 illustrates a top view of the jaw assembly 130 with the jaws in a closed configuration, and FIGS. 4-6 illustrate cross-sectional views of the jaw assembly 130 in the closed configuration. In the illustrated embodiment, the jaw assembly 130 comprises a first jaw 102 having a first clamping surface 104, a second jaw 106 having a second clamping surface 108, and a link 112. The first jaw 102 extends distally from the distal end 24 of the elongate shaft 20 (FIGS. 1-2) and is fixed to the elongate shaft 20. The second jaw 106 is pivotably coupled to the first jaw 102. In the illustrated embodiment, the second jaw 106 is pivotably coupled to the distal end 24 of the elongate shaft 20 by the link 112. For example, the link 112 can extend from a proximal end, which is pivotably coupled to the distal end 24 of the elongate shaft 20, such as with a pinned connection to a distal end, which is pivotably coupled to the second jaw 106, such as with a pinned connection.

An actuation mechanism is operably coupled to the handle assembly 40 and actuatable by the movable trigger 44 to actuate the jaw assembly 130 in an open/closed mode, in a firing mode, and in a reverse mode. The jaws 102, 106 of the jaw assembly 130 are thus actuatable between a closed configuration in which the first clamping surface 104 of the first jaw 102 is in contact with or is immediately adjacent to the second clamping surface 108 of the second jaw 106, an open configuration in which the second clamping surface 108 extends at an angle transverse to the longitudinal axis L away from the first clamping surface 104, and a stapling or firing configuration in which the second clamping surface 108 is substantially parallel to the first clamping surface 104 and is spaced therefrom. With the jaws in the stapling or firing configuration, a plurality of staples can be deployed from the first jaw 102 through tissue positioned between the first and second jaws 102, 106 and formed against the second clamping surface 108 of the second jaw 106. In some embodiments, the actuation mechanism includes an actuation member such as an actuation beam 150 that is longitudinally slideable in the elongate shaft 20. The actuation beam 150 can include a first guide 114 and a second guide 116 formed thereon.

With reference to FIG. 6, in some embodiments, a distal end of the actuation beam 150 comprises an 'I-beam' cross sectional profile with the first and second guides 114, 116 being defined by the horizontal segments of the 'I,' and the vertical segment of the 'I' comprising the actuation beam 150. In other embodiments, the actuation member or beam can have another guide configuration. For example, the guides can comprise posts, tabs, or other projections extending from the actuation member.

With reference to FIGS. 4-5, the first jaw 102 can comprise a first guide slot 118 configured to receive the first guide 114 of the actuation beam 150 in sliding engagement.

As illustrated, the first guide slot 118 can extend generally longitudinally distally from the distal end 24 of the elongate shaft 20.

With continued reference to FIGS. 4-5, in the illustrated embodiment, the link 112 can comprise a second guide slot 120 formed therein. The second guide slot 120 can extend from a proximal end to a distal end of the link 112 and can include an initial closed segment at the proximal end of the link 112, an opening segment distal the closed segment, and a firing transition segment at the distal end of the link 112.

With reference to FIGS. 4-8, the open segment has a curved or angular profile oriented such that distal sliding of the second guide 116 through the second guide slot 120 distal of the initial closed segment pivots the link 112 (and the second jaw 106 pivotably coupled thereto) away from the first jaw 102 to actuate the jaw assembly 130 from an initial closed position in which the jaw assembly has a relatively low diameter for insertion into a surgical port to an open position for receiving tissue between the first and second jaws 102, 106. In some embodiments, the link 112 can be biased away from the first jaw 102. For example, as illustrated, the jaw assembly 130 can comprise at least one spring 160 biasing the link 112 away from the first jaw 102. This bias can tend to engage the second guide 116 with the opening segment of the second guide slot 120 and position the second jaw 106 in the open position (FIGS. 7-8).

With reference to FIGS. 9-10, once tissue has been positioned between the first jaw 102 and the second jaw 106 in the open configuration at a desired stapling position, the actuation member 150 can be further advanced distally to position the jaws 102, 106 of the jaw assembly 130 in a stapling or firing configuration. Further distal movement of the actuation beam 150 advances the second guide 116 over the firing transition segment of the second guide slot 120 of the link 112 to pivot the second jaw to a position spaced apart from the first jaw a predetermined distance. The predetermined distance can be selected based on a desired tissue type for stapling in a procedure or a given staple geometry. Further distal movement of the actuation member 150 causes the second guide 116 to be received in a third guide slot 122 disposed in the second jaw 106. The third guide slot 122 can include a chamfer, radiused edge, or another transition feature to facilitate the translation of the second guide 116 distally from the second guide slot 120 to the third guide slot 122. Movement of the second guide 116 over the transition feature can further pivot the second jaw 106 such that the second clamping surface 108 is parallel to the first clamping surface 104.

As illustrated, the third guide slot 122 extends generally longitudinally along the second jaw 106 generally parallel to the second clamping surface 108 such that further distal advancement of the second guide 116 within the third guide slot 122 maintains the parallel orientation of the first and second clamping surfaces 104, 108 in the firing configuration. In other embodiments, it is contemplated that the third guide slot can extend along a curvilinear path or a path extending transversely to the second clamping surface 108 to generate a clamping force between the first and second clamping surfaces 104, 108 as the actuation member 150 is advanced distally.

With reference to FIGS. 9-10, in some embodiments, a distal end of the actuation member 150 can engage a staple driver. As the actuation member 150 is advanced distally with the jaws 102, 106 of the jaw assembly 130 in the firing position, the staple driver can deploy staples from the first jaw 102. The staple driver can include a cutting blade configured to cut tissue between rows of staples deployed by the jaw assembly.

With reference to FIGS. 11-17, another embodiment of jaw assembly 230 for use with a surgical stapler 10 is illustrated. In the illustrated embodiment, the jaw assembly 230 comprises a first jaw 202 having a first clamping surface 204 and comprising a first guide slot 218, a link 212 comprising a second guide slot 220, and a second jaw 206 having a second clamping surface 208 and comprising a third guide slot 222. An actuation member 250 or beam comprising a first guide 214 and a second guide 216 can actuate the jaw assembly 230 from the closed configuration (FIGS. 11-13), to the open configuration (FIGS. 14-15) to the firing or stapling configuration (FIGS. 16-17) in a sequence of operation substantially as described above with respect to the jaw assembly 130 of FIGS. 3-10.

With reference to FIG. 14, unlike the jaw assembly 130 of FIGS. 3-10, the second jaw 206 of the jaw assembly 230 is directly biased away from the first jaw 202. For example, in the illustrated embodiment a spring 260 is coupled to the first jaw 202 and the second jaw 206 to bias the second jaw 206 away from the first jaw. Additionally, the jaw assembly 230 includes a pivotal stop preventing excess pivoting of the second jaw 206 relative to the first jaw 202. In the illustrated embodiment, the second jaw 206 can comprise an extension such as an arm that extends proximally past the pivotal coupling of the second jaw 206 to the link 212. The extension can be sized and configured to engage the first jaw 202 when the jaw assembly 230 is positioned in the open configuration to interfere with further pivoting of the second jaw 206 away from the first jaw 202.

With reference to FIGS. 18-24, an embodiment of jaw assembly 330 for use with a surgical stapler 10 having a sliding pivot point is illustrated. In the illustrated embodiment, the jaw assembly 330 comprises a first jaw 302 having a first clamping surface 304 and comprising a first guide slot 318 and a second jaw 306 having a second clamping surface 308 and comprising a second guide slot 320. An actuation member 350 or beam comprising a first guide 314 and a second guide 316 can actuate the jaw assembly 330 from the closed configuration (FIGS. 18-20), to the open configuration (FIGS. 21-22) to the firing or stapling configuration (FIGS. 23-24) in a sequence of operation similar to those described above with respect to the jaw assemblies 130, 230.

With reference to FIGS. 20-23, in the illustrated embodiment of jaw assembly 330, the second jaw 306 is coupled to the first jaw 302 without an intercoupled link 112, 212 therebetween. Rather, the jaw assembly 330 includes a sliding pivot joint 312 that allows the second jaw 306 to pivot about a point that is translatable with respect to the first jaw 302. For example, the sliding pivot joint 312 can comprise a pivoting pin disposed in a slot formed in the first jaw 302.

With continued reference to FIGS. 20-23, the second guide slot 320 disposed in the second jaw 306 can comprise an opening segment adjacent a proximal end of the second guide slot and a firing transition segment distal the opening segment. Distal movement of the actuation member 350 distally advances the second guide 316 along the opening segment of the second guide slot 320 to slide the second jaw 306 away from the first jaw 302 and pivot the second jaw 306 into the open configuration (FIGS. 21-22). Further distal movement of the actuation member distally advances the second guide 316 past the firing transition segment and into a firing segment extending generally longitudinally along the second jaw 306 to position the jaw assembly 330 in a firing configuration (FIGS. 23-24).

With reference to FIG. 25-31, an embodiment of jaw assembly 430 with a slotted actuator for use in a surgical stapler 10 is illustrated. In the illustrated embodiment, the jaw assembly 430 comprises a first jaw 402 having a first clamping surface 404 and comprising a first guide slot 418, a link 412, and a second jaw 406 having a second clamping surface 408 and comprising a second guide slot 420. An actuation member 450 or beam comprising a first guide 414 and a second guide 416 can actuate the jaw assembly 430 from the closed configuration (FIGS. 25-27), to the open configuration (FIGS. 28-29) to the firing or stapling configuration (FIGS. 30-31) in a sequence of operation similar to those described above with respect to the jaw assemblies 130, 230.

Figure 28:
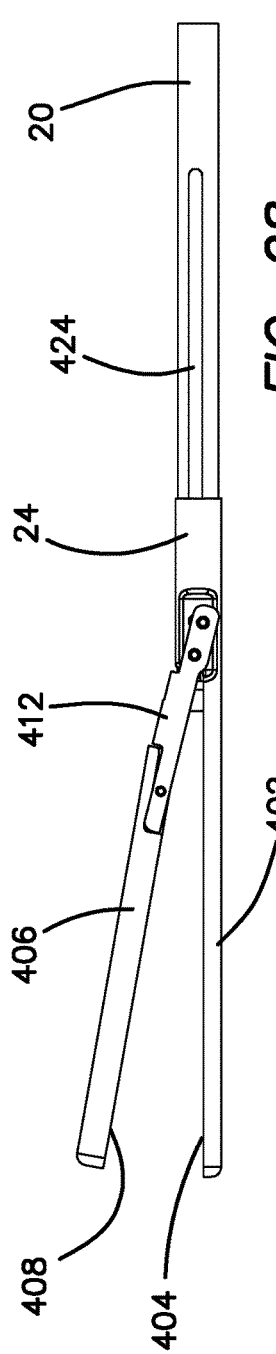
FIG. 28 is a side view of the jaw assembly of FIG. 25 with the jaws in an open configuration.
Figure 29:
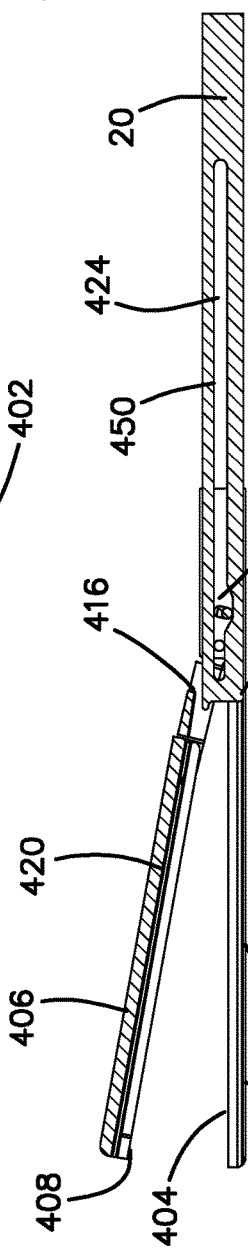
FIG. 29 is a side cross-sectional view the jaw assembly FIG. 25 with the jaws in the open configuration.
Figure 30:
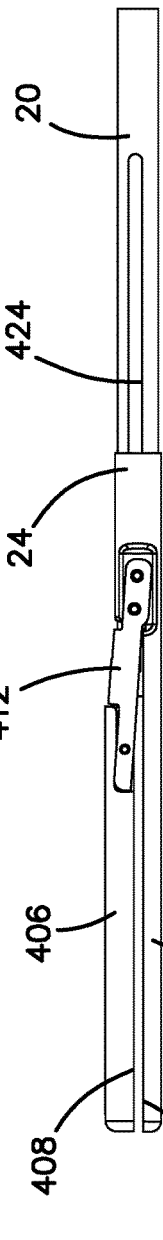
FIG. 30 is a side view of the jaw assembly of FIG. 25 with the jaws in a firing configuration.
Figure 31:
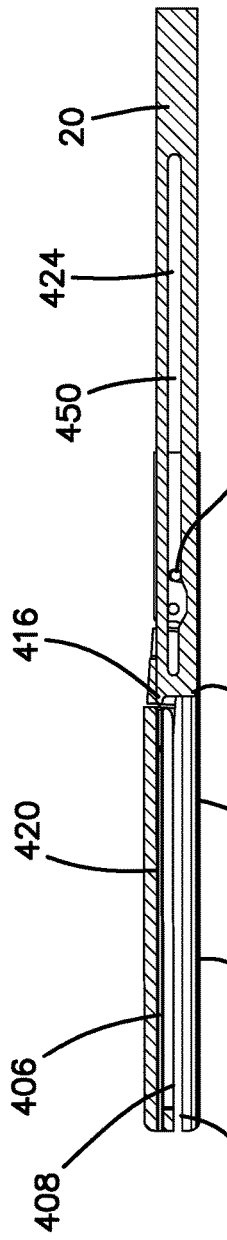
FIG. 31 is a cross-sectional side view of the jaw assembly of FIG. 25 with the jaws in the firing configuration.

With reference to FIGS. 27-29, the link 412 can include a third guide 426 thereon, such as one or more pins, tabs, or posts extending therefrom. The actuation member 450 can include a third guide slot 424 formed therein. The third guide 426 of the link 412 can be slideably engaged in the third guide slot 424. The third guide slot 424 can comprise an opening segment and a firing transition segment which extend transverse to the longitudinal axis. When the actuation member 450 is advanced distally from an initial position, the third guide 426 of the link 412 passes through the opening segment such that the link 412 is pivoted away from the first jaw 402 (FIGS. 28-29). Continued translation of the actuation member 450 advances the third guide 426 of the link 412 past the firing transition segment of the third guide slot 424 to position the second jaw 406 in the firing position (FIGS. 30-31).

With reference to FIGS. 32-38, another embodiment of jaw assembly 530 for use with a surgical stapler 10 is illustrated. In the illustrated embodiment, the jaw assembly 530 comprises a first jaw 502 having a first clamping surface 504 and comprising a first guide slot 518, a link 512 comprising a second guide slot 520, and a second jaw 506 having a second clamping surface 508 and comprising a third guide slot 522. An actuation member 550 or beam comprising a first guide 514 and a second guide 516 can actuate the jaw assembly 530 from the closed configuration (FIGS. 32-34), to the open configuration (FIGS. 35-36) to the firing or stapling configuration (FIGS. 37-38) in a sequence of operation similar to those described above with respect to the jaw assemblies 130, 230, 430.

With reference to FIGS. 34-36, in the illustrated embodiment, the actuation member 550 can include a first guide 514 positioned at a distal end of a first arm or extension and a second guide positioned at a distal end of a second arm or extension. The first and second arms can be flexibly coupled to one another such that a distance between the first guide 514 and the second guide 516 can be varied. The first and second arms can be biased away from one another. Advantageously, the variable spacing of the first guide 514 and second guide 516 can allow positioning of the third guide slot 522 in a position relatively close to an outer surface opposite the second clamping surface 508 of the second jaw 506. Accordingly, additional working space in the second jaw adjacent the second clamping surface can be freed by positioning the third guide slot 522 closer to the outer surface.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of claims which follow.

What is claimed is:

1. A surgical stapler comprising:
   an elongate shaft having a proximal end and a distal end and defining a longitudinal axis between the proximal end and the distal end;
   a handle assembly disposed at the proximal end of the elongate shaft;
   an actuation mechanism actuatable by the handle assembly, the actuation mechanism comprising an actuation beam extending through at least a portion of the elongate shaft;
   a jaw assembly disposed at the distal end of the elongate shaft, the jaw assembly comprising:
      a first jaw defining a first clamping surface;
      a second jaw defining a second clamping surface; and
      a plurality of staples positioned in the first jaw;
   wherein the jaw assembly is actuatable by longitudinal movement of the actuation beam between a closed position in which the first clamping surface contacts the second clamping surface, an open position in which the second clamping surface extends at an angle transverse to the first clamping surface, and a stapling position in which the first clamping surface extends parallel to the second clamping surface and is spaced apart from the second clamping surface, and
   wherein the jaw assembly further comprises a link having a proximal end pivotably coupled to the proximal end of the elongate shaft and a distal end pivotably coupled to the second jaw.

2. A surgical stapler comprising:
   an elongate shaft having a proximal end and a distal end and defining a longitudinal axis between the proximal end and the distal end;
   a handle assembly disposed at the proximal end of the elongate shaft;
   an actuation mechanism actuatable by the handle assembly, the actuation mechanism comprising an actuation member extending through at least a portion of the elongate shaft, the actuation member comprising a first guide and a second guide thereon;
   a jaw assembly disposed at the distal end of the elongate shaft, the jaw assembly comprising:
      a first jaw extending distally from the distal end of the elongate shaft, the first jaw comprising a first guide slot extending longitudinally therein;
      a link having a proximal end and a distal end, the link comprising a second guide slot having a ramped opening profile formed therein, and the proximal end of the link being pivotably coupled to the distal end of the elongate shaft;
      a second jaw extending distally from the distal end of the link and pivotably coupled to the distal end of the link, the second jaw comprising a third guide slot extending longitudinally therein; and
      a plurality of staples disposed in the first jaw;
   wherein the first guide is slideable in the first guide slot and the second guide is slideable in the second guide slot and the third guide slot, and wherein translation of the second guide distally over the ramped opening profile of the second guide slot pivots the link away from the first jaw to define an open position of the jaw assembly.

3. The surgical stapler of claim 2, wherein the link is pivotally biased away from the first jaw.

4. The surgical stapler of claim 3, wherein the second jaw is pivotally biased towards the first jaw.

5. The surgical stapler of claim 4, wherein the link and the second jaw are configured to interfere with pivotal motion of the second jaw with respect to the link to limit pivoting of the second jaw towards the first jaw.

* * * * *